(12) United States Patent
French et al.

(10) Patent No.: US 6,375,625 B1
(45) Date of Patent: Apr. 23, 2002

(54) IN-LINE SPECIMEN TRAP AND METHOD THEREFOR

(75) Inventors: C. Kenneth French, Cranfills; Garrett L. Barker, Meridian, both of TX (US); Melvin E. Levinson, Miami, FL (US)

(73) Assignee: Scion Valley, Inc., Meridian, TX (US)

( * ) Notice: Subject to any disclaimer, the term of this patent is extended or adjusted under 35 U.S.C. 154(b) by 0 days.

(21) Appl. No.: 09/852,417

(22) Filed: May 11, 2001

Related U.S. Application Data
(60) Provisional application No. 60/241,467, filed on Oct. 18, 2000.

(51) Int. Cl.$^7$ .............................. A61B 5/00; B65D 81/00
(52) U.S. Cl. ...................................................... 600/573
(58) Field of Search ...................... 606/45, 46; 600/573, 600/571, 565, 564, 562, 563, 575; 604/319, 22; 73/863.23

(56) References Cited

U.S. PATENT DOCUMENTS

| | | | | |
|---|---|---|---|---|
| 3,855,997 A | * | 12/1974 | Sauer ........................... | 600/573 |
| 4,643,197 A | * | 2/1987 | Greene et al. ............... | 600/575 |
| 5,335,671 A | * | 8/1994 | Clement ....................... | 604/22 |
| 5,575,293 A | * | 11/1996 | Miller et al. ................ | 600/565 |
| 5,810,806 A | * | 9/1998 | Ritchart et al. ............... | 606/45 |

* cited by examiner

*Primary Examiner*—John P. Lacyk
*Assistant Examiner*—Brian Szmal
(74) *Attorney, Agent, or Firm*—Robert C. Kain, Jr.; Fleit Kain

(57) ABSTRACT

The in-line specimen trap operates in conjunction with a suction or irrigation line and a second line leading to a surgical site. The trap includes a specimen container, a cap coupled to the specimen container and an operator controlled, multi-modal valve disposed in or on the cap. The valve includes at least a bypass passage and a container input port and a container output port. The bypass passage limits flow exclusively between the first and second lines, that is, between the suction/irrigation line and the line leading to the surgical site. The position of an operator control interface determines the selection of the bypass mode or trap and collection mode. The method establishes, under operator control, a bypass channel between the first and second lines channels under operator control, the specimen fluid and debris from the second line through the specimen container to the first line, and, closes the specimen container after the channeling step.

37 Claims, 4 Drawing Sheets

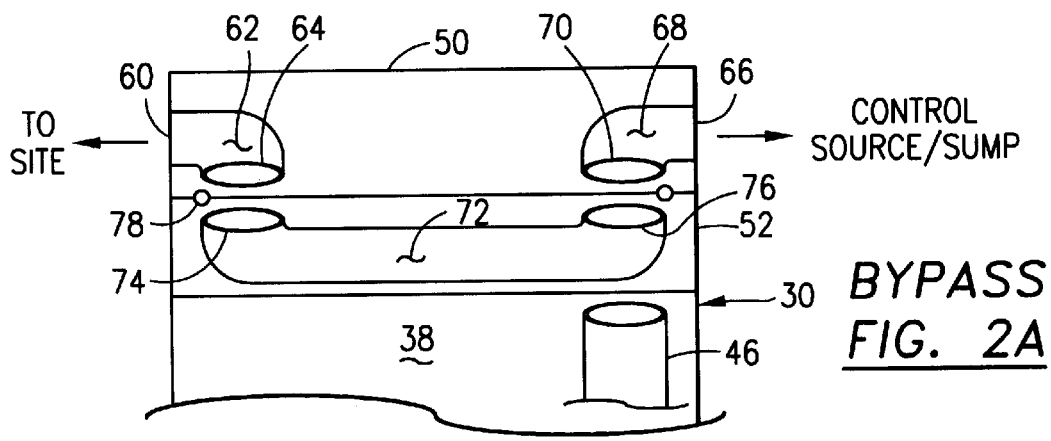
BYPASS FIG. 2A
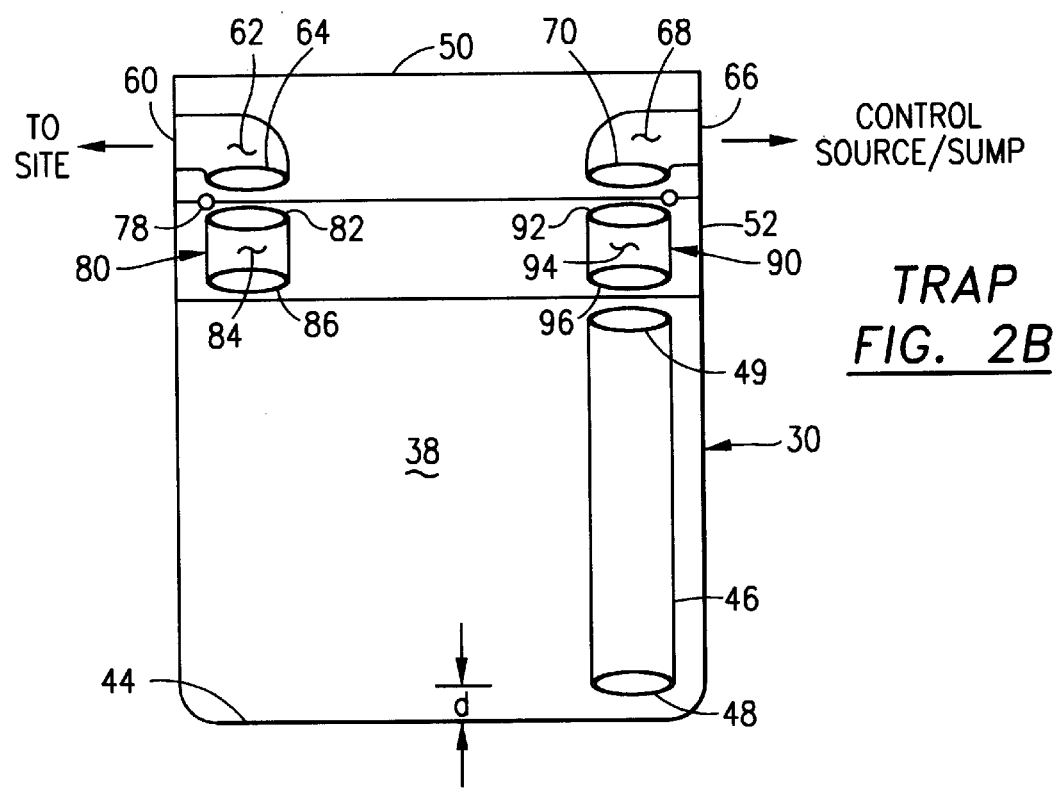
TRAP FIG. 2B
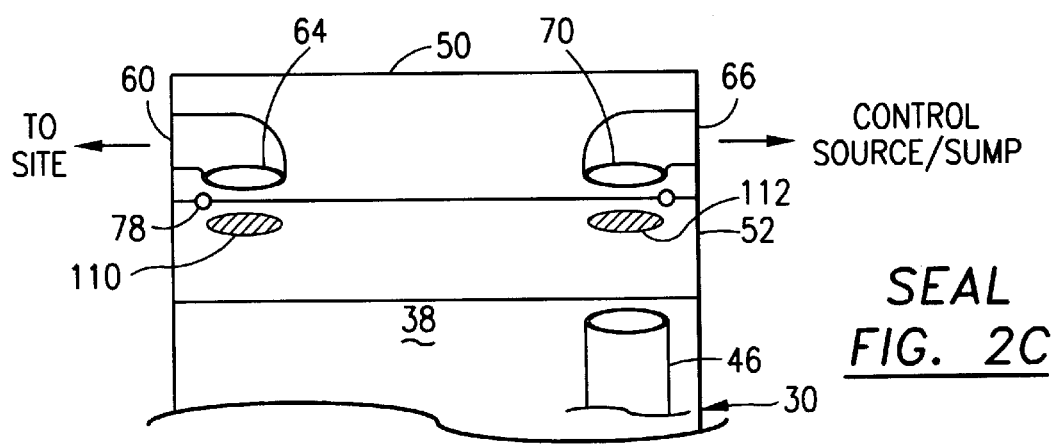
SEAL FIG. 2C

IN-LINE SPECIMEN TRAP AND METHOD THEREFOR

This is a regular patent application based upon and claiming the benefit of provisional patent application Ser. No. 60/241,467 filed Oct. 18, 2000.

The present invention relates to an in-line specimen trap, a biomedical device utilized in conjunction with a controlled irrigation/suction system proximal to a surgical site, and a method therefor.

BACKGROUND OF THE INVENTION

During certain types of surgical procedures, the surgical site (for example, the site of the wound) is irrigated with irrigation fluid and fluid and debris is suctioned away from the surgical site via a suction line. Irrigation fluid is delivered to this irrigation site via an irrigation line. Many times, the suction and irrigation lines are coupled to a valve control system which is controlled by the surgeon or other medical professional. The output of the valve system, opposite the suction line and irrigation line, is coupled to a probe which leads to the surgical site. The valve is sometimes called a trumpet valve. Various trumpet valves are illustrated and discussed in U.S. Pat. No. 6,062,429 to West et al.; U.S. Pat. No. 6,148,857 to West et al. and U.S. Pat. No. 6,171,072 B1 to West et al. In general, these trumpet valves and other irrigation/suction valves operate by permitting the surgeon to control either the degree of irrigation or the degree of suction delivered through the probe or line leading to the surgical site.

Sometimes there is a need to collect specimens from the surgical site.

OBJECTS OF THE INVENTION

It is an object of the present invention to provide an in-line specimen trap adapted to be used in conjunction with the controlled delivery of suction and/or irrigation and a surgical probe or line leading to the surgical site.

It is another object of the present invention to provide an in-line specimen trap that has multiple operating modes, one of which is a bypass mode permitting substantially direct coupling between the suction or irrigation line (dependent upon the valve control) and the line leading to the surgical site and a second control mode wherein fluids and particulate debris from the surgical site are cycled through a specimen container.

It is an additional object of the present invention to have an in-line specimen trap with a third control mode in which the suction/irrigation line and the line leading to the surgical site are blocked off thereby permitting the trap to be uncoupled from these lines and carried away. Preferably, specimen fluid and/or particulate debris remain in the specimen trap container.

It is a further object of the present invention to enable the specimen trap to be used to infuse liquid to the surgical site.

SUMMARY OF THE INVENTION

The in-line specimen trap operates in conjunction with a first line carrying controlled suction or irrigation and a second line leading to a surgical site. The trap includes a specimen container, a cap coupled to the specimen container and an operator controlled, multi-modal valve disposed in or on the cap. The valve includes at least a bypass passage and a container input port and a container output port. The bypass passage limits flow exclusively between the first and second lines, that is, between the suction/irrigation line and the line leading to the surgical site. The container input and output ports permit flow through the container via the first and second lines. The position of an operator control interface determines the selection of the bypass mode or trap and collection mode through the container input and output ports. In an enhanced embodiment, the specimen trap has a third mode of operation (the first mode of operation being the bypass operation and the second mode of operation being flow through the container via the input and output ports) wherein, in the third control mode, the suction/irrigation line and the second line leading to the surgical site are blocked. In the third control mode, the in-line specimen trap can be removed and withdrawn from the suction/irrigation line and the line leading to the surgical site. Preferably, the valve for the specimen trap includes a valve manifold with the bypass and input and output ports and an operator interface on the cap of the specimen trap. The valve manifold is typically disposed in the cap. The operator rotates the cap relative to the specimen container and thereby selects the bypass mode, the trap mode or the seal (blocking) mode. The method of selectively (a) trapping specimen fluid and debris and (b) permitting suction and irrigation flow includes providing a specimen container, establishing, under operator control, a bypass channel between the first and second lines (the suction/irrigation line and the leading to the surgical site), channeling, under operator control, the specimen fluid and debris from the second line through the specimen container to the first line, and, closing the specimen container after the channeling step. Fluid infusion to the surgical site involves loading the container with the infusion substance and flushing the container with irrigant and outputting the resultant mixture to the surgical site line.

BRIEF DESCRIPTION OF THE DRAWINGS

Further objects and advantages of the present invention are found in the detailed description of the preferred embodiments when taken in conjunction with the accompanying drawings in which:

FIGS. 2A, 2B and 2C diagrammatically and graphically illustrate the bypass control mode, the trap control mode and the seal control mode in accordance with the principles of the present invention;

DETAILED DESCRIPTION OF THE PREFERRED EMBODIMENTS

The present invention relates to an in-line specimen trap and a method for selectively (a) trapping specimen fluid and debris and (b) permitting suction and irrigation flow between a suction/irrigation line and a second line leading to a surgical site.

Figure 1:
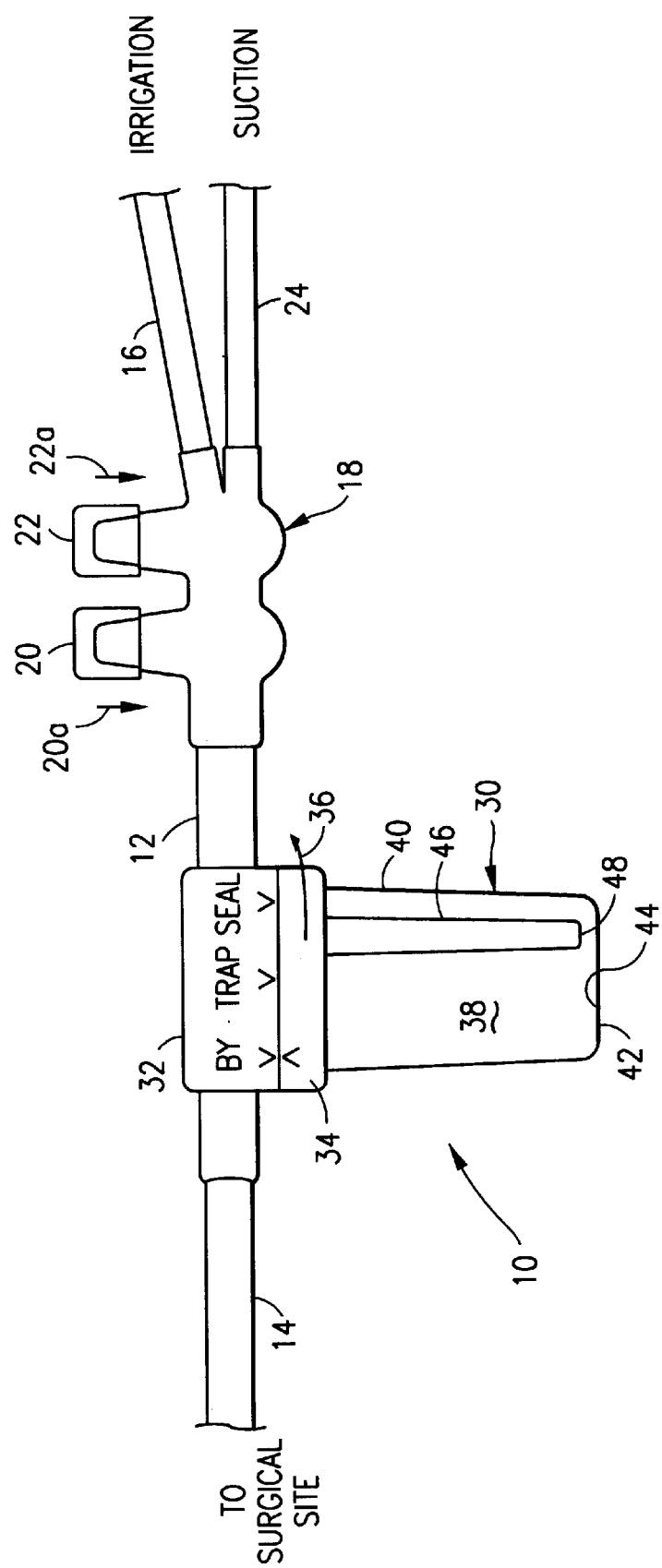
FIG. 1 diagrammatically illustrates the in-line specimen trap coupled between the suction/irrigation line and a second line leading to a surgical site and further diagrammatically illustrates a trumpet valve and the suction line and the irrigation line coupled to the suction/irrigation control valve.

FIG. 1 diagrammatically illustrates in-line specimen trap 10 coupled between a suction/irrigation or first line 12 and a second line 14 leading to a probe (not shown) at a surgical site. Irrigation fluid is provided via an irrigation line 16 to a valve system 18. In the illustrated embodiment in FIG. 1, valve system 18 is a trumpet valve having a pair of user control interfaces 20, 22 which control the degree of irrigation fluid to suction/irrigation line 12 (disposed on the proximal side of control valve 18) or suction on line 12. The term "distal" refers to objects remotely disposed from the surgical site whereas the term "proximal" refers to items relatively closer to the surgical site. Suction on line 12 is obtained by depression of one of the controls 20, 22 due to the opening of an internal valving mechanism (not shown) and the presence of a partial vacuum on suction line 24. At the distal end of suction line 24 (not shown) is a sump for discharged fluid, debris and particulate. Actuator valve controls 20, 22 are depressed by the operator as shown by arrows 20a and 22a. Other types of suction/irrigation control valves could be utilized.

In-line specimen trap 10 includes a specimen container 30, a cap 32 and an operator controlled, multi-modal valve. In the illustrated embodiment, the operator control is a rotating control actuator surface 34. The operator selects one of three control modes: bypass mode (illustrated in FIG. 1), trap control mode or seal control mode by rotating operator interface 34 in the direction shown by arrow 36. As explained later, in the bypass control mode, suction or irrigation is provided between line 12 and line 14 exclusively through the value system in the specimen trap. In the trap control mode, suction and irrigation passes through interior 38 of specimen container 30. In the third or sealed control mode, the valve system in the in-line specimen trap 10 blocks line 14 leading to the surgical site and blocks suction/irrigation line 12. This enables specimen trap 10 to be decoupled from lines 12, 14 and withdrawn from the surgical site.

Specimen container 30 includes container wall 40 and a lower container wall 42. Walls 40, 42 include interior surfaces. Particularly, lower wall 42 includes interior surface 44. In-line specimen trap 10 also includes a leader tube 46 disposed in the interior of specimen container 30. Leader tube 40 has a port or opening 48 somewhat adjacent or proximate interior surface 44 of lower wall 42.

In a preferred embodiment, specimen container 30 is transparent. Transparent container 30 enables the medical professional to determine the amount of fluid and debris collected in the specimen container during the trap control mode. Debris, mainly particulate, falls to lower interior surface 44 of container 30.

FIGS. 2A, 2B and 2C diagrammatically and graphically illustrate the valve disposed, in the preferred embodiment, in the cap 32 of in-line specimen trap 10. It should be noted that the valve could be disposed on top of cap 32 and an intermediate cap, between upper surface 32 and specimen container 30 could be provided with closeable through passages.

In FIGS. 2A–2C, cap 32 includes an upper, stationary member 50 and a lower, rotating member 52. Similar numerals designate similar items in FIGS. 2–2C. FIG. 2A shows the in-line specimen trap in the bypass control mode. Stationary cap member 50 has a port 60 that is coupled to line 14 (FIG. 1). An interior passage way 62 leads to an interior port 64. Stationary cap member 50 also includes port 66, interior passage way 68 and interior port 70. Port 66 is coupled to section/irrigation line 12. Hence, in FIG. 2A, port 60 is coupled to line 14 which leads to the surgical site and port 66 is coupled to a line 12 which leads to the controlled irrigation source or controlled suction line to the sump. The term "control" refers to the controlled nature of irrigation flow or degree of suction provided the operator by valve control system 18 shown in FIG. 1 or other similar valving control system.

Movable member 52 includes a bypass passage 72 communicating with ports 74 and 76. In the bypass control mode shown in FIG. 2A, port 74 is aligned with port 64 and hence is in communication with the surgical site via line 14 (FIG. 1). Port 76 is in communication with port 70 and hence is in communication with suction/irrigation line 12, valving system 18 and irrigation supply line 16 and suction vacuum line 24. See FIG. 1. A seal 78 may be provided at a peripheral location between cap members 50, 52. In a working embodiment, stationary cap member 50 is cylindrical and movable cap member 52 is cylindrical. Hence, seal 78 is disposed radially beyond mating ports 64, 74 leading to the surgical site and ports 70, 76 leading to the suction/irrigation line and control source and sump. In the bypass control mode, specimen container 30 is not coupled to fluid ports 60, 66 in stationary cap member 50. Hence, bypass passage 72 limits flow exclusively between the first and second lines, that is, suction/irrigation line 12 and surgical site line 14.

FIG. 2B diagrammatically illustrates the trap control mode. In order to position the containment system in the trap control mode, movable cap member 52 is rotated in direction 36 shown in FIG. 1 relative to the stationary cap member 50. Operator control surface 34 (FIG. 1) is coupled to movable cap member 52. In the trap control mode shown in FIG. 2B, movable cap member 52 includes a first input port 80 having interior port 82, interior passage 84 and container port 86. Port 82 mates with port 64 of stationary cap member 50. Chamber port 86 is in communication with interior 38 of specimen container 30. Movable cap member 52 also includes an output port 90. Output port 90 includes an interior port 92, a through passage 94 and a chamber port 96. In a preferred embodiment, chamber port 96 is permanently coupled to or mounted with leader tube 46. In operation, suction is applied at port 66 of stationary cap member 50. This draws fluid and particulate debris or other materials from the surgical site, into port 60, through ports 64 and 82 and chamber port 86 (that is, input port system 80) and into interior chamber 38 of specimen container 30. Since leader tube 46 has an upper opening 49 in communication with port 96, fluid and, to some extent, particulate debris is suctioned into opening 48 of leader tube 46, through ports 49, 96, intermediate passage 94, through ports 92 (defining output port system 90), port 70 and out port 66. Opening 48 of leader tube 46 is spaced an appropriate distance d apart from lower interior wall 44, that is, a distance sufficient to trap a requisite amount of fluid and/or particulate debris in the lower regions of interior 38 of specimen container 30.

In a preferred embodiment, specimen chamber 30 rotates concurrently with movable cap member 52. Hence, there may be a permanent continuity between interior passage 94 and the interior of leader tube 46. Another words, ports 96 and 49 may be eliminated. FIGS. 2A–2C and 3 graphically illustrate the invention. Alternatively, specimen container 30 can be statically mounted to stationary cap member 50 and movable cap member 52 could rotate to open and close bypass passage 72 and input port 80 and output port 90. In this construction, leader tube 46 moves with respect to output port 90. A further static cap is mounted on container 30 in this alternative embodiment. Further in all embodiments, container 30 may be threadably mounted on cap system 50, 52.

FIG. 2C shows a sealed control mode. Movable cap member 52 has been rotated, in a preferred embodiment, such that interior port 64 (leading to the surgical site via line 14 (FIG. 1)) and interior port 70 (leading to suction/irrigation line 12 and the controlled irrigation source and controlled suction and sump) are independently blocked. In order to show this blocking or sealing of interior ports 64, 70, the figure shows cross-hatched areas 110, 112. Movable member 52 may or may not have sealing seats 110, 112.

Figure 3:
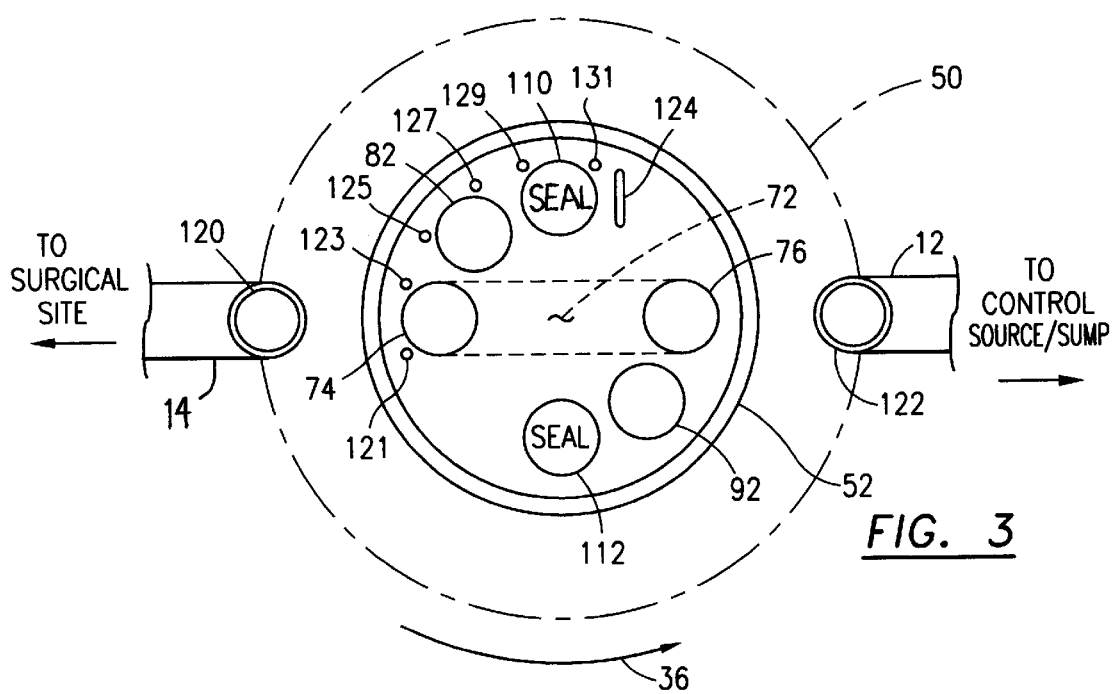
FIG. 3 graphically illustrates the multi-modal valve in the cap of the in-line specimen trap.

FIG. 3 graphically illustrates the rotating valve manifold defined by movable cap member 52. Line 14 leads to the surgical site. Suction/irrigation line 12 leads to control valve 18 (FIG. 1) and independent irrigation line 16 and suction line 24 (FIG. 1) which is the controlled irrigation source and controlled suction or vacuum to the sump. Stationary cap member 50 is graphically illustrated by the dash dot dash line in FIG. 3. Port 74 is illustrated graphically as being in communication with opening 120 of line 14 leading to the surgical site. Port 76 is graphically illustrated in communication with opening 122 of irrigation/suction line 12. Ports 74 and 76 communicate with bypass passage 72.

When movable member 52 is rotated in direction shown by arrow 36, ports 82, 92 align with openings 120, 122 of lines 14 and 12. This represents the trap control mode shown in FIG. 2B. A plurality of detents 121, 123, 125, 127, 129 and 131 cooperate with similar or complementary detents on stationary cap member 50 in order to provide a tactile response to the user when the user rotates movable member 52 relative to stationary member 50. Detents 121, 123 permit accurate alignment of ports 74, 76 with openings 120, 122. Detents 125, 127 permit accurate alignment of ports 82, 92 with openings 120, 122. Of course, ports 74, 76 align with interior ports 64, 68 shown in FIG. 2A. The detents are operative to permit the operator to "feel" the alignment of bypass passage 72 and the alignment of ports 74, 76 with interior ports 64, 68. Since ports 64, 68 lead to ports 60, 66 (FIG. 2A) and those latter ports are described as being connected to lines 14, 12, FIG. 3 graphically illustrates the rotatable valve manifold.

When movable cap member 52 is further rotated in direction 36, seal regions 110, 112 are placed to close ports leading to openings 120, 122. This positioning of seals 110, 112 is tactily noted by the user based on detents 129, 131. A stop 124 limits further movement in direction 36. The counter stop (not shown) is disposed at an appropriate position on stationary cap member 50. Another complementary stop is placed on the static cap to limit rotation in a clockwise direction from the position shown in FIG. 3. Hence, stop 124 is configured to move from the twelve o'clock position shown in FIG. 3 to the nine o'clock position based upon the maximum arcuate rotation in direction 36 of movable cap member 52.

Figure 4:
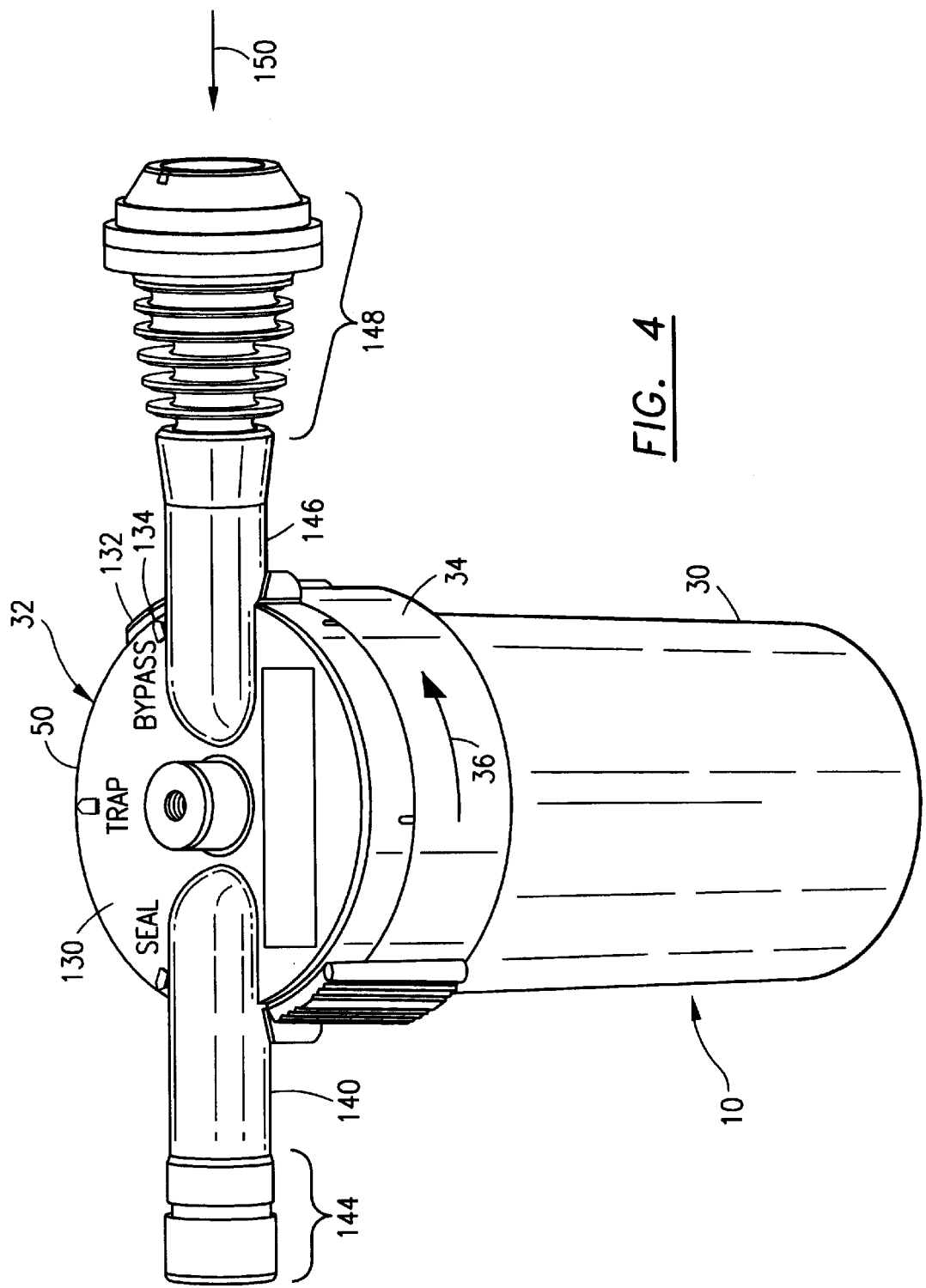
FIG. 4 diagrammatically illustrates a perspective view of the in-line specimen trap.

FIG. 4 shows a perspective view of a working embodiment of the in-line specimen trap 10. Cap 32 includes a stationary cap member 50. The movable cap member 52 is not shown in FIG. 4 but is interior to cap 32. User control surface 34 is coupled in a appropriate manner to movable cap member 52. Upper cap surface 130 includes indicia for the bypass, trap and seal control modes. Operator control surface 34 includes a tab 132 and an indicia marker 134 which points to complementary markers at bypass control position (marker 134), trap position and seal position. This enables the operator to visually confirm the control position of the in-line specimen trap.

In order to facilitate coupling and uncoupling from the surgical probe and the control valve 18 (FIG. 1), in-line specimen trap 10 includes a port extension 140 and a fluid coupling member 144. Fluid coupling member 144 fits into the proximal end of the trumpet control valve 18 shown in FIG. 1. Another port extender 146 is configured to a slide on line 14 of the probe via accordion coupler 148. The surgical probe is inserted into coupler 148 in the direction shown by arrow 150.

Coupling joints 144, 148 fluidly seal to the lines at either end of the trap 10.

Specimen container 30 may be designed to screw and unscrew from the cap assembly 32 if necessary.

A wide variety of multi-modal valves can be used in conjunction with the in-line specimen trap. Essentially, the specimen trap valve must have at least two positions, a bypass position and a position which permits communication to the interior of specimen container 30. In other words, a two position valve must have a bypass passage which exclusively limits flow from line 14 leading to the surgical site through the specimen trap valve and to the suction/irrigation line 12. The other control position must permit flow into specimen container 30 through a container input port and permit flow out of container 30 via container output port. A three position valve is shown and described herein. Although a rotating valve manifold is shown in FIGS. 1–3 other types of valves can be utilized.

Figure 5A:
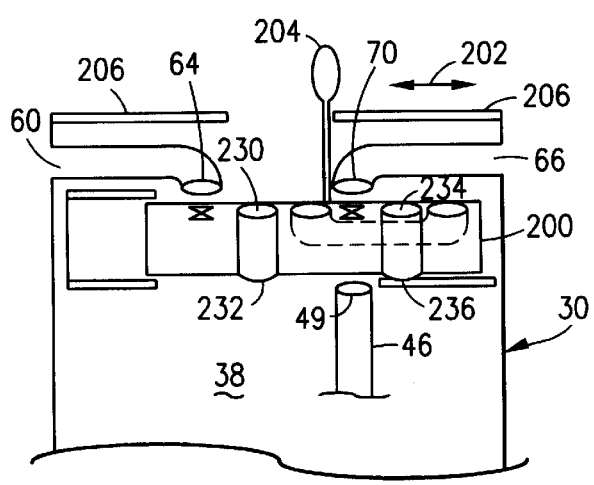
FIGS. 5A and 5B diagrammatically illustrate a linear valve and valve manifold in accordance with the principles of the present invention.
Figure 5B:
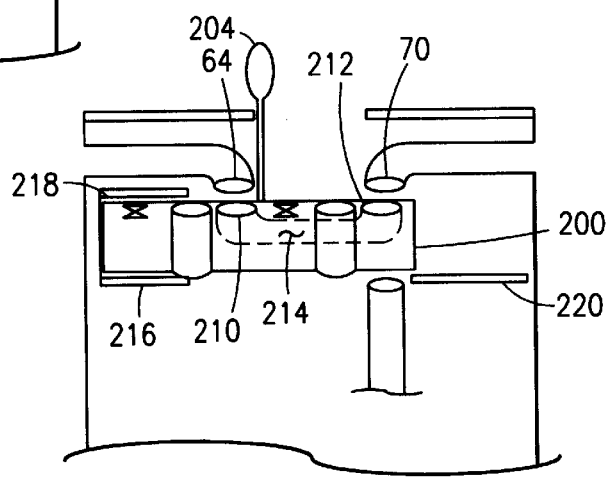

FIGS. 5A and 5B show a linear valve. The linear valve in FIGS. 5A, 5B includes a valve manifold 200 which moves in the direction show by double headed arrow 202 based upon the user actuating user interface 204. Interface 206 represents any typical actuator surface. Ports 60, 66 are coupled to the surgical line 14 and suction/irrigation line 12 as described above in connection with FIG. 2A. In the position shown in FIG. 5A, interior ports 64, 70 communicate with primary ports 60, 66 but flow through the system is blocked off by port closures or seats shown by the Xs on valve manifold 200.

In contrast in FIG. 5B, the user has linearly moved user actuator surface 204 and valve manifold 200 to the opposite linear position. In this position, port 64 is adjacent and in communication with port 210. Port 70 is in communication with port 212. This permits suction, debris and irrigation fluid flow exclusively through bypass channel 214. Valve manifold 200 moves on tracks 216, 218 and 220. In the intermediate position not shown in the figures, port 64 is aligned with port 230. This permits fluid and debris to flow from port 60, through the internal passage way, out of port 64, into port 230 and out of port 232 and into the interior 38 of specimen container 30. Also in that position, port 234 is in communication with port 70, and port 23 is in communication with opening 49 of leader tube 46. This permits fluid flow and debris flow up leader tube 44, through port 236, through the interior port of the valve manifold 200, out of port 234, into port 270, out of port 266, through the control valve 18 (FIG. 1) and into suction line 24.

The rotating valve shown in FIGS. 2A–2C and 3 rotatably positions the ports for the bypass, trap and seal position. In FIG. 5A–5B, the valve manifold moves linearly to open and close ports in a controlled manner. Flow and blockage of the primary ports 60, 66 is established in the specimen trap and through the valve manifold as discussed earlier.

The in-line specimen trap device is intended to be inserted in-line with the suction/irrigation probe used in conjunction with trumpet valves. The probe, utilized by a medical professional at the surgical site, is removed and the specimen trap is attached to the valve. The probe is then re-attached to the specimen trap. The purpose of the specimen trap is to enable the physician to capture particulate for analysis that is suctioned through the probe.

The specimen trap in one preferred embodiment consists of two main components: the molded plastic in-line connection with a valve and potentially a filter and the removable, transparent plastic specimen cap. The valve mechanism is activated by rotating the plastic cap. There are three positions: by-pass, trap and sealed. In the bypass mode, any fluid or particles suctioned from the surgical site will not be deposited into the cap. Fluid and debris from the site are passed directly through the trumpet valve into the suction system. In the trap position, everything suctioned first goes through the specimen cup, where particulate debris are trapped. In the sealed position, the specimen cup is sealed to keep its contents from spilling and the device can be removed from the trumpet valve.

When the specimen trap is attached to the trumpet valve as described above, it is initially set in the bypass position. In this position, suction and irrigation modes function normally. When the cup is rotated to the trap position, it is ready to be used to capture specimen. If the trap is to be used in the normal mode, the cup can be rotated back to the bypass position. Once the necessary particulate specimen is accumulated, the cup is rotated to the sealed position for removal from the trumpet valve and transport to the laboratory.

Another use of the in-line specimen trap is to infuse medication. To accomplish this function, the specimen cup is initially filled with whatever is to be infused into the patient. When set in trap mode, and the trumpet valve activated to introduce irrigant, the contents of the specimen cup is carried into the patient.

The claims appended hereto are meant to cover modifications and changes within the scope and spirit of the present invention.

What is claimed is:

1. An in-line specimen trap adapted to be coupled between first line carrying controlled suction or irrigation and a second line leading to a surgical site, said trap comprising:
   a specimen container;
   a cap coupled to said specimen container;
   an operator controlled multi-modal valve disposed in or on said cap, said multi-modal valve having at least a bypass passage, said bypass passage limiting flow exclusively between said first and second lines, and a container input port and container output port, said input and output ports permitting flow through said container via said first and second lines.

2. An in-line specimen trap as claimed in claim 1 wherein said multi-modal valve includes an operator control shifting flow between said bypass passage and said input and output ports.

3. An in-line specimen trap as claimed in claim 1 wherein said bypass passage is fluidly coupled to said first and second pines in a first control mode and said input and output ports lead to and from said specimen container and are fluidly coupled to said first and second lines and in a second control mode.

4. An in-line specimen trap as claimed in claim 1 wherein said specimen container is defined by container walls and one of said walls defines a lower interior surface, the specimen trap including a leader tube coupled to said output port, said leader tube extending proximately towards said lower interior surface of the specimen container wall.

5. An in-line specimen trap as claimed in claim 1 wherein said bypass passage in said multi-modal valve defines a first flow path, said input and output ports, in conjunction with said specimen container, define a second flow path, said multi-modal valve having a third path blocking flow between said first and second lines.

6. An in-line specimen trap as claimed in claim 5 wherein said bypass passage is fluidly coupled to said first and second lines via said first flow path in a first control mode and said input and output ports lead to and from said specimen container and are fluidly coupled to said first and second lines via said second flow path and in a second control mode and said first and second lines are closed in the blocking third path in a third control mode.

7. An in-line specimen trap as claimed in claim 6 wherein said multi-modal valve includes an operator control shifting and blocking flow between said first, second and third paths, respectively.

8. An in-line specimen trap as claimed in claim 7 wherein said operator control includes a rotating operator interface.

9. An in-line specimen trap as claimed in claim 8 including a rotating valve manifold defining said first, second and third paths, said manifold coupled to said rotating operator interface.

10. An in-line specimen trap as claimed in claim 9 wherein said manifold is mounted in said cap.

11. An in-line specimen trap as claimed in claim 1 wherein said cap is detachably coupled to said specimen container.

12. An in-line specimen trap as claimed in claim 1 wherein said specimen container is a elongated, transparent container and said cap is mounted on the top of the container.

13. An in-line specimen trap as claimed in claim 7 wherein said operator control includes a linearly movable operator interface.

14. An in-line specimen trap as claimed in claim 13 including a linearly movable valve manifold defining said first, second and third paths, said manifold coupled to the linear operator interface.

15. An in-line specimen trap as claimed in claim 14 wherein said manifold is mounted in said cap.

16. An in-line specimen trap as claimed in claim 1 wherein said bypass passage in said multi-modal valve defines a first flow path, and said input and output ports, in conjunction with said specimen container, define a second flow path.

17. An in-line specimen trap as claimed in claim 16 wherein said bypass passage is fluidly coupled to said first and second pines via said first flow path in a first control mode and said input and output ports lead to and from said specimen container and are fluidly coupled to said first and second lines via said second flow path and in a second control mode.

18. An in-line specimen trap as claimed in claim 17 wherein said multi-modal valve includes an operator control shifting flow between said first and second flow paths.

19. An in-line specimen trap as claimed in claim 18 wherein said operator control includes one of a rotating operator interface and a linearly movable operator interface and the specimen trap includes one of a rotating valve manifold and a linearly movable valve manifold, said manifold defining said first and second flow paths and said manifold coupled to said operator interface.

20. An in-line specimen trap as claimed in claim 19 wherein said manifold is mounted in said cap.

21. An in-line specimen trap as claimed in claim 2 wherein said bypass passage is fluidly coupled to said first and second pines in a first control mode and said input and output ports lead to and from said specimen container and are fluidly coupled to said first and second lines and in a second control mode.

22. An in-line specimen trap as claimed in claim 21 wherein said specimen container is defined by container walls and one of said walls defines a lower interior surface, the specimen trap including a leader tube coupled to said output port, said leader tube extending proximately towards said lower interior surface of the specimen container wall.

23. An in-line specimen trap as claimed in claim 22 wherein said bypass passage in said multi-modal valve defines a first flow path, said input and output ports, in conjunction with said specimen container, define a second flow path, said multi-modal valve having a mode blocking flow between said first and second lines.

24. An in-line specimen trap as claimed in claim 23 wherein said bypass passage is fluidly coupled to said first and second pines via said first flow path in a first control mode and said input and output ports lead to and from said specimen container and are fluidly coupled to said first and second lines via said second flow path and in a second control mode and said first and second lines are closed in the blocking third path in a third control mode.

25. An in-line specimen trap as claimed in claim 24 wherein said operator control shifts and blocks flow between said first, second and third paths, respectively.

26. An in-line specimen trap as claimed in claim 25 wherein said operator control includes a rotating operator interface.

27. An in-line specimen trap as claimed in claim 26 including a rotating valve manifold defining said first, second and third paths, said manifold coupled to said rotating operator interface.

28. An in-line specimen trap as claimed in claim 27 wherein said manifold is mounted in said cap.

29. An in-line specimen trap as claimed in claim 28 wherein said cap is detachably coupled to said specimen container.

30. An in-line specimen trap as claimed in claim 29 wherein said specimen container is a elongated, transparent container and said cap is mounted on the top of the container.

31. An in-line specimen trap as claimed in claim 25 wherein said operator control includes a linearly movable operator interface.

32. An in-line specimen trap as claimed in claim 31 including a linearly movable valve manifold defining said first, second and third paths, said manifold coupled to the linear operator interface.

33. An in-line specimen trap as claimed in claim 32 wherein said manifold is mounted in said cap.

34. A method of selectively (a) trapping specimen fluid and debris and (b) permitting suction and irrigation flow between a first line carrying controlled suction or irrigation and a second line leading to a surgical site, the method comprising:

providing a specimen container;

establishing, under operator control, a bypass channel between said first and second lines;

channeling, under operator control, said specimen fluid and debris from said second line through said specimen container to said first line; and, closing said specimen container after said channeling step.

35. A method as claimed in claim 34 including blocking flow, under operator control, at said first line and at said second line.

36. A method as claimed in claim 34 wherein said establishing step occurs under at a first operative control point and said channeling step occurs at a second operative control point.

37. A method as claimed in claim 35 wherein said establishing step occurs under at a first operative control point, said channeling step occurs at a second operative control point and said blocking occurs at a third control point.

* * * * *